(12) United States Patent
Abascal

(10) Patent No.: US 7,922,661 B2
(45) Date of Patent: Apr. 12, 2011

(54) ECHOGRAPHIC PROBE WTIH SECTOR SCANNING USING A TRANSDUCER CAPABLE OF COMING INTO CONTACT WITH THE STRUCTURE TO BE EXAMINED

(75) Inventor: Jean Abascal, Arcueil (FR)

(73) Assignee: Quantel Medical, Clermont-Ferrand (FR)

( * ) Notice: Subject to any disclaimer, the term of this patent is extended or adjusted under 35 U.S.C. 154(b) by 942 days.

(21) Appl. No.: 10/590,566

(22) PCT Filed: Feb. 25, 2005

(86) PCT No.: PCT/FR2005/000465
§ 371 (c)(1),
(2), (4) Date: Aug. 24, 2006

(87) PCT Pub. No.: WO2005/089652
PCT Pub. Date: Sep. 29, 2005

(65) Prior Publication Data
US 2007/0276249 A1    Nov. 29, 2007

(30) Foreign Application Priority Data

Feb. 27, 2004  (FR) ..................................... 04 02209

(51) Int. Cl.
*A61B 8/00* (2006.01)

(52) U.S. Cl. ......... 600/439; 600/456; 600/437; 600/446

(58) Field of Classification Search ................... 600/439, 600/407, 409, 410, 437
See application file for complete search history.

(56) References Cited

U.S. PATENT DOCUMENTS

| | | | |
|---|---|---|---|
| 3,753,219 A | 8/1973 | King, Jr. | |
| 4,605,009 A * | 8/1986 | Pourcelot et al. | 600/109 |
| 4,762,002 A * | 8/1988 | Adams | 73/625 |
| 5,123,418 A * | 6/1992 | Saurel et al. | 600/459 |
| 5,357,963 A * | 10/1994 | Mayol et al. | 600/446 |
| 5,487,388 A | 1/1996 | Rello et al. | |
| 5,630,416 A | 5/1997 | Uchikura et al. | |
| 6,213,948 B1 | 4/2001 | Barthe et al. | |
| 6,287,261 B1 | 9/2001 | Surosa et al. | |

FOREIGN PATENT DOCUMENTS

| | | |
|---|---|---|
| EP | 0 403 349 A1 | 12/1990 |
| WO | WO 94/27501 A1 | 12/1994 |

* cited by examiner

*Primary Examiner* — Long V Le
*Assistant Examiner* — Joel F Brutus
(74) *Attorney, Agent, or Firm* — Browdy and Neimark, PLLC

(57) ABSTRACT

The inventive probe comprises a tubular body (1, 2) that accommodates a transducer (11), which emits a focused incident ultrasonic wave toward structures to be examined and which receives the ultrasonic waves reflected by these structures. This transducer (11) is coupled to actuating means (4), comprises a piezoelectric assembly (15) capable of focusing the emitted beams and, adjacent to this assembly, comprises a spherical layer (20) made of a material that ensures a good transmission of the ultrasonic waves.

10 Claims, 3 Drawing Sheets

ECHOGRAPHIC PROBE WTIH SECTOR SCANNING USING A TRANSDUCER CAPABLE OF COMING INTO CONTACT WITH THE STRUCTURE TO BE EXAMINED

BACKGROUND OF THE INVENTION

1. Field of the Invention

The invention relates to an echographic probe with sector scanning using a transducer capable of coming into contact with the structure to be examined.

It is notably but not exclusively applied to echography of eye structures.

2. Description of the Prior Art

Generally, it is known that in opthalmology, 2-D echography at 10 MHz is used in current practice for exploring the anatomy and pathologies of eye structures and more particularly that of the posterior pole (retina, optical nerve, vitreous).

The technique of the probes uses sector scanning, with which probes may be obtained of small sizes, comparatively to bar probes.

In order to perform this type of scan, echographic probes are used, including an open tubular casing in its front portion and the inner volume of which is divided into two compartments by a sealed partition, i.e.:

a rear compartment which extends on the side of the bottom of the casing: this compartment comprises motorization and power supply circuits for the control and processing parts of the apparatus, a front compartment adjacent to the aperture of the casing, which contains a mobile transducer as well as all or part of its actuation mechanism.

The aperture of the front compartment is usually closed by a flexible or hard sealed membrane, in order to obtain a sealed interior space containing a coupling liquid which should have high transmissibility for ultrasonic waves.

This membrane which is intended to come into contact with the eye of the patient, should be made in a biocompatible material which does not damp high frequency ultrasound. It confines the coupling liquid while allowing the eye to be protected from any accidental contact with mechanical parts, i.e., notably the transducer and/or its actuation mechanism. Now, these are results which are difficult to obtain, which explains the invention's advantage of reducing these problems to the making of the transducer itself, i.e., at the source of ultrasound, so as to be able to act more easily on the global features of the transducer.

Echographic apparatuses of this type nevertheless prove to have a certain number of drawbacks. Indeed:

Before reaching the eye, the ultrasonic wave focused by the concave curvature of the piezoelectric element of the transducer, has to pass through several layers of material having different properties and this, with different propagation velocities, the path of these waves inside these layers varying according to the (variable) position of the transducer.

This causes variations in the focal length of the transducer and inaccuracies in the obtained echographic image.

Moreover, it is seen that in the case of a high frequency transducer (from 15 MHz), liquids and membranes become increasingly absorptive. Consequently, the frequencies which effectively penetrate the tissues are much less than the frequencies emitted by the transducer.

Thus, as an example, for a transducer emitting with a frequency of 20 MHz, the transmitted central frequency will be 18 MHz with a loss of 10 dB.

Within the scope of open probes, all these drawbacks are suppressed since the coupling medium consists in a water bath which has good acoustic properties. However, the transducer performs its motion at a very small distance from the structure to be examined and even if it has a circular shape, its edges are aggressive and accordingly, it is not possible to suppress any risk of trauma by accidental contact of the transducer with the eye (scratching of the cornea by the circular edge of the transducer).

OBJECT OF THE INVENTION

Accordingly, more particularly, the object of the invention is to suppress these drawbacks.

SUMMARY OF THE INVENTION

For this purpose it proposes an echographic probe with sector scanning comprising a tubular body at least partially housed in its front end, a transducer designed so as to emit an incident ultrasonic wave focused in the direction of the structures to be examined and to receive ultrasonic waves generated by these structures under the effect of this incident wave, this transducer being associated with actuation means so as to be able to perform displacements, at least partially in rotation in order to obtain a sector scan of the structures to be examined.

According to the invention, the transducer comprises a piezoelectric assembly having a power of focusing emitted beams while having at its end, an axisymmetric surface, the generatrix of which has a curved shape and the director axis of which corresponds to the axis of rotation of the transducer, this surface being intended to come into contact with the structure to be examined. This curved shape may be circular in order to obtain a toric shape or a spherical shape.

By means of these arrangements, the presence of any aggressive edge in the transducer portion which may come into contact with the eye is suppressed. The first problem of the open probes is thereby solved, as the transducer will no longer be a member capable of damaging the eye and this, even in the case of a wrong move by the clinician. On the other hand, the material used is such that it withstands all decontamination protocols with soakings.

With the direct transducer/tissue-to-be-examined contact, the aforementioned inaccuracies may be avoided. Only the application of a gel on the tissues is required for providing good transmission of ultrasound.

The frequencies which effectively penetrate into the tissues are actually those emitted by the transducer.

BRIEF DESCRIPTION OF THE DRAWINGS

Embodiments of the invention will be described hereafter, as non-limiting examples, with reference to the appended drawings wherein.

DESCRIPTION OF THE PREFERRED EMBODIMENTS

Figure 1:
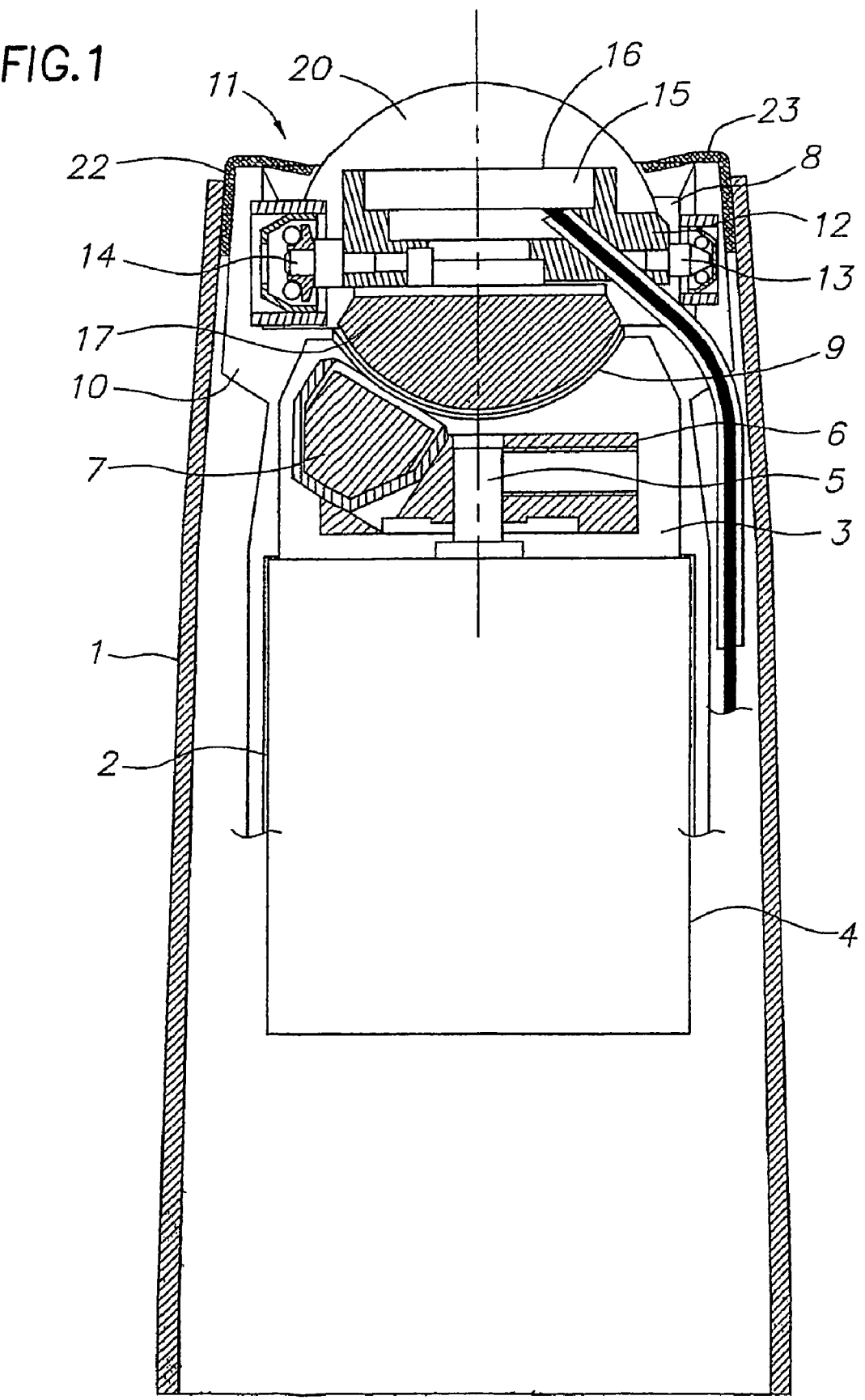
FIG. 1 is an axial section of a probe with a spherical transducer.
Figure 2:
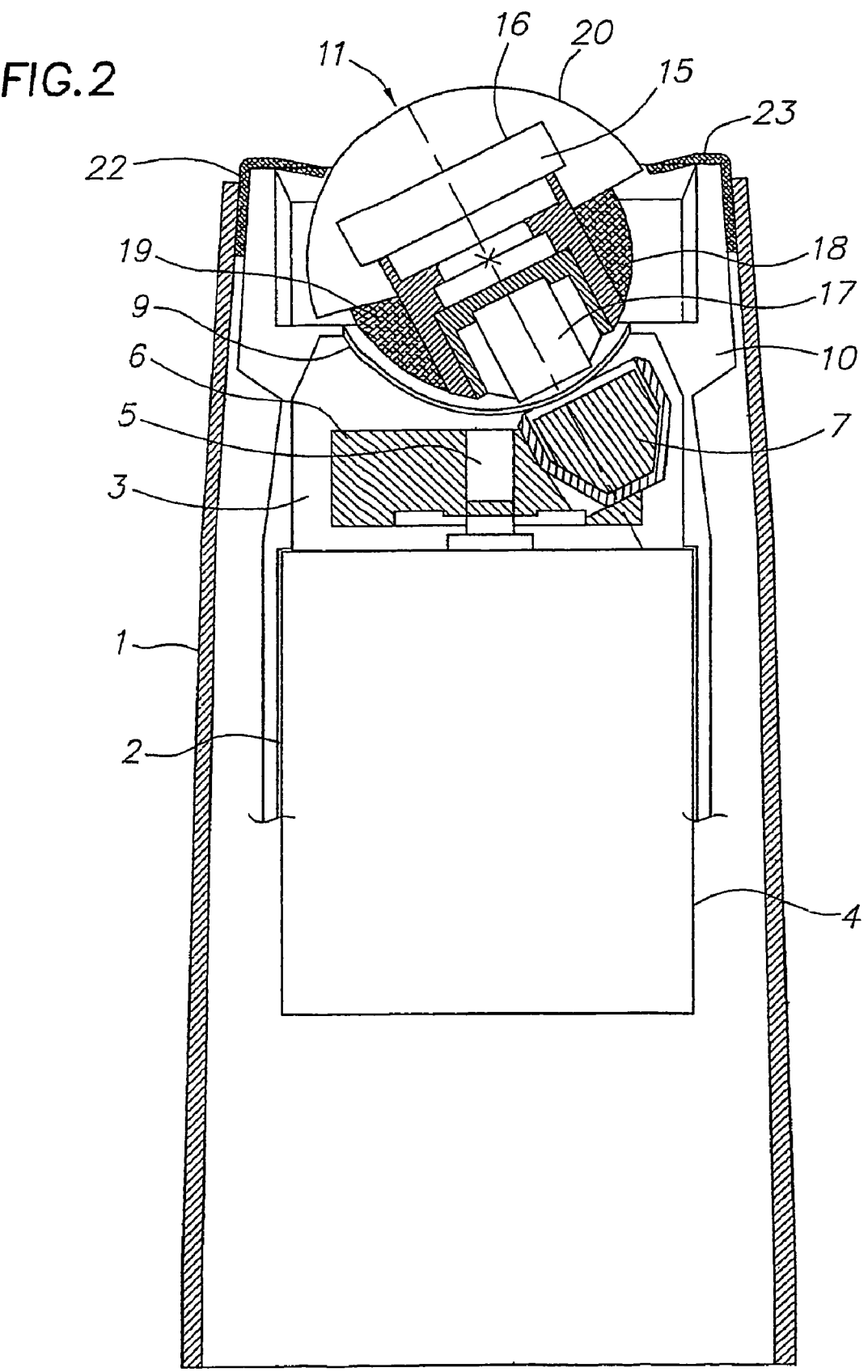
FIG. 2 is a 90° axial section of the section illustrated in FIG. 1.

In the example illustrated in FIGS. 1 and 2, the probe has a double-walled tubular body, partly illustrated, including an outer wall 1, for example in stainless steel, and an inner wall 2, for example in plastic.

The inner wall 2 delimits two successive compartments, i.e.:
- a rear compartment 3, in which is housed a coaxial gear motor 4, the central shaft 5 of which drives into rotation a driving rotating plate 6 bearing a permanent magnet 7, and
- a front compartment 8, open at its end opposite to the posterior compartment 3.

The separation between both compartments 3, 8, is provided by a spherical partition 9, obtained by molding or machining with the inner wall 2 and the concavity of which is directed towards the front compartment 8. This spherical partition 9 is found in the extension of an inner flange 10 forming a throat between both chambers 3, 8.

The permanent magnet 7 housed in a cavity of the rotating plate 6 has a cylindrical and frustro-conical shape obliquely centered relatively to the drive axis 5 of the motor 4 and the large base of which extends tangentially to the spherical partition 9.

Inside the front chamber 8, a spherical transducer 11 is rotatably mounted, including a main supporting part 12 with a substantially cylindrical shape and a staged bore, rotatably mounted on the inner wall 2 by means of two coaxial pins 13, 14, centered perpendicularly to the main axis of the part 12. In this example, both pins 13, 14 are borne by bearings mounted in coaxial cylindrical housings provided in the inner wall 2.

This main supporting part 12 comprises on one side at a predetermined distance from the axis of both pins 13, 14, a bore discontinuity delimiting a cavity open outwards in which a piezoelectric assembly 15 is positioned, having a outward focusing power and its outer shape 20 of which is spherical.

On the side of the axis of the pins, opposite to the element 15, the main supporting part forms a shell which delimits a cavity into which a drive permanent magnet 17 is engaged, having a spherical surface centered perpendicularly to the axis of the pins 13, 14, thereby fitting to the shape of the spherical partition 9.

On the lateral sides of the main supporting part 12, which extend parallel to the axis of the pins 13, 14, two respective side magnets 18, 19 are attached (FIG. 2), intended for cooperating with a Hall effect detector in order to determine the angular position of the transducer 11. These side magnets 18, 19 have an outer spherical shape concentric with the transducer 11.

According to the invention, the front part of the transducer 11 (located on the side of the piezoelectric element, relatively to the axis of the pins) is coated with a molded material layer 20 with high transmissibility for ultrasonic waves emitted by the piezoelectric assembly 15.

In this example, this layer 20, which has a spherical outer surface coaxial with the transducer 11, stops at a height of about 5° relatively to the equatorial plane of the transducer 11. This layer 20 coats the transducer sufficiently so as to provide contact with the structures to be explored during the whole rotation.

The seal between the outer 7 and inner 2 walls in the vicinity of the orifice, is for example provided by a elastomeric gasket 22 with a cylindrical shape including a radial flange 23 directed towards the inside, which will cover the end of the inner wall 2 in order to rest with its inner edge on the spherical surface of the layer 20.

With this gasket 22, it is therefore possible to avoid introduction of liquid or solid material inside the front chamber 8 of the probe 11.

By means of the arrangements described earlier, by supplying electrical energy to the motor 4, the rotary plate 6 and therefore the magnet is caused to rotate, the magnet performing a circular trajectory around the longitudinal axis of the probe in the immediate vicinity of the spherical partition 9.

Under the effect of the rotating magnetic field generated by the magnet 7, the permanent magnet 17 is subject to an attractive/repulsive force which causes an alternating rotary movement of the spherical transducer 11 around the axis of the pins 13, 14. The transducer 11 performs a sector scan, the angular position of which is detected by means of the action of the side magnets 18, 19 on the Hall effect detector.

Figure 3:
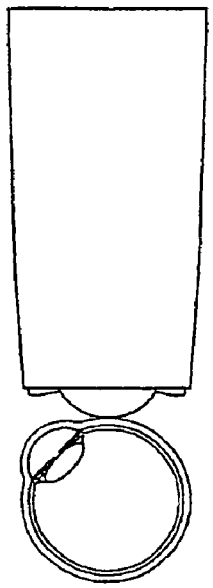
FIG. 3 is a sectional view with a reduced scale of a probe of the type shown in FIGS. 1 and 2 applied on the eye of a patient.

The front part of the spherical transducer 11, which emerges from the flange 23 of the elastomeric gasket 22, may be directly put into contact with the eye, as indicated in FIG. 3. Only a slight gel layer may be applied on the eye to provide good transmission of ultrasound and to improve the sliding between the eye and the spherical transducer.

Of course, the invention is not limited to the embodiment described earlier.

Thus, for example, the probe 25 (FIG. 4) may comprise a spherical transducer 26 rotatably mounted around an axis parallel to the longitudinal axis of the body of the probe 25.

Figure 4:
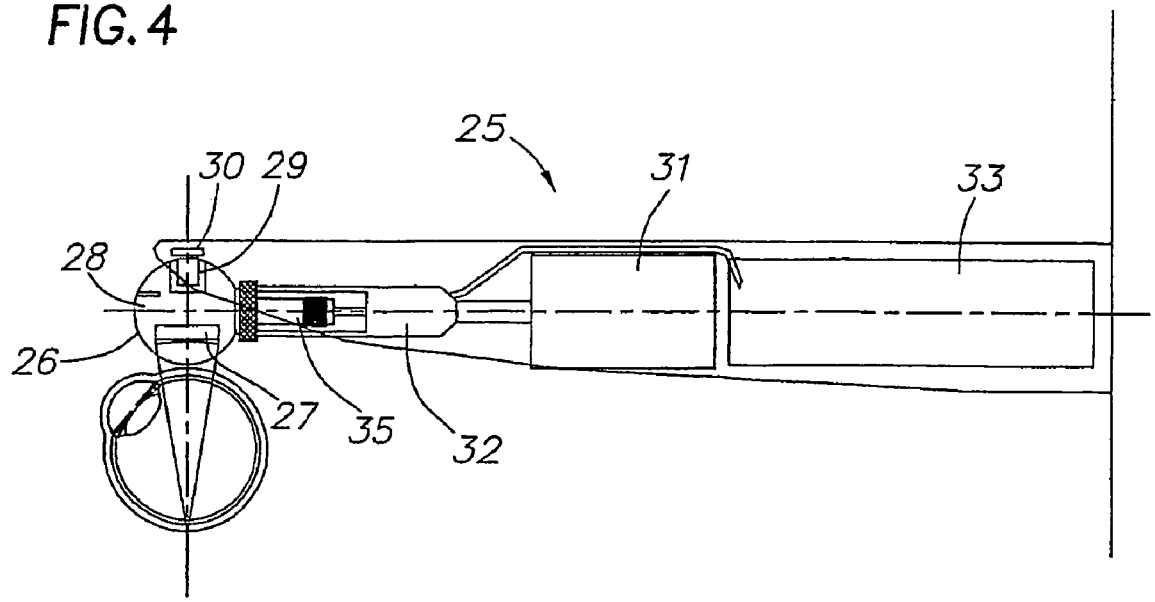
FIG. 4 is a schematic illustration of an alternative embodiment of the probe according to the invention.

In this case, the piezoelectric element 27 may be centered perpendicularly to the axis of rotation of the transducer 26 as illustrated in FIG. 4.

In this case, the piezoelectric assembly 27 is coated in a spherical part 28 in a material providing proper transmission of ultrasonic waves.

Driving the assembly 27 into rotation is here provided by means of a motor 31 coaxial with the probe and the output shaft thereof connected to the transducer by means of a transmission component 32, provides the mechanical attachment of the spherical part 28.

The electrical connection of the active component is achieved by the screw connector 35 of the SMC or equivalent type, accessible through the recessed portions of the transmission element 32. A permanent magnet 29 facing a Hall effect sensor 30 integral with the casing of the probe 25, enables the position information to be sent back to the card 33 controlling the motor for an alternating reciprocal movement.

Taking into account the fact that the angular sector scanned by the transducer 27 is centered perpendicularly to the axis of the probe 25, the front end of the body of the probe 25 ends on one side as a slightly curved bevel so as to delimit an oblique aperture and to expose the useful area of the transducer 27 which should be applied to the eye. The advantage of this solution consists in that during echography, vision of the eye of the patient by the operator is only very partially hidden by the probe 25 (only by its front end). The hand which holds the probe 25 will be outside the field of vision, which was not the case in the example described earlier.

Moreover, the movements of the transducer are not limited to simple alternating rotational movements. Indeed, these movements may be of the arc-shaped type. In this case, the transducer may be mounted on an actuated device for example of the type of the one which is described in Patent Application No. 02 05780 as of May 7, 2002, on behalf of the applicant.

In this case, the spherical shape of a transducer provides considerable limitation of the risk of any accident.

The invention claimed is:

1. An echographic probe with sector scanning comprising a tubular body at least partly housed in its front end, a transducer configured to emit an incident ultrasonic wave focused towards a structure to be examined and to receive ultrasonic waves generated by the structures under the effect of the incident ultrasonic wave, this transducer being rotatably mounted inside the tubular body around an axis of rotation and being coupled with actuating means so as to be able to perform displacements at least partly in rotation relatively to the tubular body in order to obtain a sector scan of the structure to be examined, wherein the transducer comprises a piezoelectric assembly having power for focusing the ultrasonic waves and adjacent to the piezoelectric assembly, a layer made in a material providing good transmission of ultrasonic waves, this layer having, opposite to said piezoelectric assembly, a convex axisymmetric outer surface, the generatrix of which has a curved shape and the director axis of which corresponds to the axis of rotation of the transducer so as to be able to come into contact with the structure to be examined.

2. The probe according to claim 1, wherein the aforesaid generatrix has a circular shape.

3. The probe according to claim 1, wherein the aforesaid axisymmetric surface is spherical.

4. The probe according to claim 1, wherein the transducer comprises a permanent magnet cooperating with a Hall effect sensor integral with the tubular body in order to provide detection of the position of said transducer.

5. The probe according to claim 1, wherein the transducer is rotatably mounted on the tubular body along an axis of rotation and comprises a first permanent magnet located opposite the piezoelectric assembly relatively to said axis, contactless actuation of said transducer being provided by means of a second permanent magnet mounted on a rotary driving plate which performs a circular trajectory centered perpendicularly to said axis of rotation.

6. The probe according to claim 5, wherein the aforesaid transducer and the aforesaid drive plate provided with the aforesaid second permanent magnet are positioned in two compartments of the body, separated by a partition, respectively.

7. The probe according to claim 6, wherein the aforesaid partition has a spherical shape concentric with the aforesaid transducer.

8. The probe according to claim 1, wherein said tubular body is with double walls, the seal between both walls at the orifice of the body crossed by the transducer is provided by a cylindrical gasket including a radial flange directed inwards, the interior edge of which will rest on the spherical surface of the transducer.

9. The probe according to claim 1, comprising at least a partially spherical transducer mounted around an axis parallel to the longitudinal axis of the tubular body of the probe, the transducer including a piezoelectric element centered perpendicularly to the axis of rotation of the transducer, the front end of the tubular body of the probe ending as a bevel in order to delimit an oblique aperture exposing a useful area of the transducer centered transversally to the longitudinal axis of the tubular body.

10. The probe according to claim 1, wherein the aforesaid transducer is mounted on an actuation mechanism with which an arc-shaped scan may be obtained.

* * * * *